US009763859B2

(12) United States Patent
Motornov et al.

(10) Patent No.: US 9,763,859 B2
(45) Date of Patent: Sep. 19, 2017

(54) ANHYDROUS EMULSIONS CONTAINING POLYLYSINE AND POLAR MODIFIED POLYMER

(71) Applicant: L'OREAL, Paris (FR)

(72) Inventors: Mikhail Motornov, Clark, NJ (US); Hy Si Bui, Piscataway, NJ (US); Jean-Thierry Simonnet, Mamaroneck, NY (US); Christopher Pang, New York, NY (US)

(73) Assignee: L'OREAL, Paris (FR)

( * ) Notice: Subject to any disclaimer, the term of this patent is extended or adjusted under 35 U.S.C. 154(b) by 591 days.

(21) Appl. No.: 14/236,259

(22) PCT Filed: Oct. 1, 2012

(86) PCT No.: PCT/US2012/058316
§ 371 (c)(1),
(2) Date: Jan. 30, 2014

(87) PCT Pub. No.: WO2013/049821
PCT Pub. Date: Apr. 4, 2013

(65) Prior Publication Data
US 2014/0194535 A1 Jul. 10, 2014

Related U.S. Application Data

(60) Provisional application No. 61/541,457, filed on Sep. 30, 2011.

(51) Int. Cl.
*A61Q 1/00* (2006.01)
*A61K 8/06* (2006.01)
*A61K 8/31* (2006.01)
*A61Q 1/02* (2006.01)
*A61Q 1/04* (2006.01)
*A61Q 1/06* (2006.01)
*A61Q 1/10* (2006.01)
*A61K 8/81* (2006.01)
*A61K 8/88* (2006.01)
*A61K 8/64* (2006.01)

(52) U.S. Cl.
CPC .................. *A61K 8/06* (2013.01); *A61K 8/31* (2013.01); *A61K 8/64* (2013.01); *A61K 8/8111* (2013.01); *A61K 8/8164* (2013.01); *A61K 8/88* (2013.01); *A61Q 1/00* (2013.01); *A61Q 1/02* (2013.01); *A61Q 1/04* (2013.01); *A61Q 1/06* (2013.01); *A61Q 1/10* (2013.01); *A61K 2800/31* (2013.01)

(58) Field of Classification Search
None
See application file for complete search history.

(56) References Cited

U.S. PATENT DOCUMENTS

| 6,048,520 | A | * | 4/2000 | Hoshowski | A61K 8/11 424/70.1 |
|---|---|---|---|---|---|
| 6,080,394 | A | | 6/2000 | Lin et al. | |
| 6,177,071 | B1 | | 1/2001 | Lin et al. | |
| 6,221,927 | B1 | | 4/2001 | Lin et al. | |
| 8,551,461 | B2 | | 10/2013 | Bui et al. | |
| 8,597,621 | B2 | | 12/2013 | Bui et al. | |
| 8,597,626 | B2 | | 12/2013 | Bui et al. | |
| 8,609,079 | B2 | | 12/2013 | Bui et al. | |
| 8,652,451 | B2 | | 2/2014 | Bui et al. | |
| 8,663,609 | B2 | | 3/2014 | Bui et al. | |
| 8,663,667 | B2 | | 3/2014 | Bui et al. | |
| 2004/0009132 | A1 | * | 1/2004 | Wang | A61K 8/062 424/63 |
| 2007/0031361 | A1 | | 2/2007 | Herrmann et al. | |
| 2008/0095725 | A1 | | 4/2008 | Nguyen et al. | |
| 2008/0095726 | A1 | | 4/2008 | Nguyen et al. | |
| 2008/0095729 | A1 | | 4/2008 | Nguyen et al. | |
| 2008/0097070 | A1 | | 4/2008 | Nguyen et al. | |
| 2009/0035244 | A1 | | 2/2009 | Rando et al. | |
| 2010/0322876 | A1 | | 12/2010 | Nguyen et al. | |
| 2010/0330012 | A1 | | 12/2010 | Bui et al. | |
| 2010/0330015 | A1 | | 12/2010 | Bui et al. | |
| 2010/0330016 | A1 | | 12/2010 | Bui et al. | |
| 2010/0330017 | A1 | | 12/2010 | Bui et al. | |
| 2010/0330022 | A1 | | 12/2010 | Bui et al. | |
| 2010/0330024 | A1 | | 12/2010 | Bui et al. | |
| 2011/0020254 | A1 | | 1/2011 | Bui et al. | |
| 2011/0020255 | A1 | | 1/2011 | Bui et al. | |
| 2011/0020256 | A1 | | 1/2011 | Bui et al. | |
| 2011/0020259 | A1 | | 1/2011 | Bui et al. | |
| 2011/0020260 | A1 | | 1/2011 | Bui et al. | |
| 2011/0021681 | A1 | | 1/2011 | Bui et al. | |
| 2011/0021683 | A1 | | 1/2011 | Bui et al. | |
| 2011/0150802 | A1 | | 6/2011 | Bui et al. | |
| 2011/0150806 | A1 | | 6/2011 | Bui et al. | |

(Continued)

FOREIGN PATENT DOCUMENTS

WO WO 2009/086036 A1 7/2009
WO WO2009085783 * 7/2009 ............... A61K 8/00

OTHER PUBLICATIONS

Polylysine. https://web.archive.org/web/20101116003609/http://truthinaging.com/ingredients/polylysine. Published: Nov. 16, 2010.*

(Continued)

*Primary Examiner* — Jyothsna Venkat
(74) *Attorney, Agent, or Firm* — Oblon, McClelland, Maier & Neustadt, L.L.P.

(57) ABSTRACT

The present invention generally relates to anhydrous emulsions containing an oil-soluble polar modified polymer and polylysine.

10 Claims, No Drawings

(56) References Cited

U.S. PATENT DOCUMENTS

| | | |
|---|---|---|
| 2011/0223123 A1 | 9/2011 | Bui et al. |
| 2011/0280819 A1 | 11/2011 | Bui et al. |
| 2011/0280820 A1 | 11/2011 | Bui et al. |
| 2011/0286949 A1 | 11/2011 | Bui et al. |
| 2011/0286950 A1 | 11/2011 | Bui et al. |
| 2011/0286951 A1 | 11/2011 | Bui et al. |
| 2011/0286954 A1 | 11/2011 | Bui et al. |
| 2011/0293550 A1 | 12/2011 | Bui et al. |
| 2012/0003169 A1 | 1/2012 | Bui et al. |
| 2012/0004327 A1 | 1/2012 | Bui et al. |
| 2012/0020907 A1 | 1/2012 | Bui et al. |
| 2012/0107263 A1 | 5/2012 | Bui et al. |
| 2012/0171140 A1 | 7/2012 | Bui et al. |
| 2014/0004069 A1 | 1/2014 | Bui et al. |
| 2014/0037565 A1 | 2/2014 | Bui et al. |

OTHER PUBLICATIONS

U.S. Appl. No. 14/343,979, filed Mar. 10, 2014, Motornov, et al.
U.S. Appl. No. 14/241,361, filed Feb. 26, 2014, Motornov, et al.
U.S. Appl. No. 14/241,753, filed Feb. 27, 2014, Motornov, et al.
International Search Report issued Mar. 19, 2013 in PCT/US2012/058327.
International Search Report issued Mar. 29, 2013 in PCT/US2012/058318.
International Search Report issued Mar. 29, 2013 in PCT/US2012/058321.
International Search Report issued Mar. 29, 2013, in PCT/US2012/058316, filed Oct. 1, 2012.

* cited by examiner

ANHYDROUS EMULSIONS CONTAINING POLYLYSINE AND POLAR MODIFIED POLYMER

CROSS-REFERENCE TO RELATED APPLICATIONS

This application claims the benefit of priority from U.S. Provisional Application Ser. No. 61/541,457, filed Sep. 30, 2011, the entire contents of which is hereby incorporated by reference.

FIELD OF THE INVENTION

The present invention relates to emulsions comprising anhydrous solvent-in-oil (S/O) emulsion comprising at least one oil-soluble polar modified polymer and at least one polylysine. Such compositions can possess improved properties and characteristics such as, for example, stability, increased long wear and anti-smudging properties.

DISCUSSION OF THE BACKGROUND

A key trait of cosmetic compositions, such as for example makeup and sunscreens, are long wear and low cost. In particular, consumers are looking for affordable make up products that offers transfer resistance, water resistance, wear comfort; the products should maintain of a fresh look throughout the day. These properties are generally dependent on the properties of silicone resins and silicone elastomers that are typically used but have negative drawbacks such as high costs and formulation difficulties, particularly with water. High water content make up products with a possibility to encapsulate actives is beneficial and can provide additional skin hydration.

The state of the art technology in makeup for texture and non-transfer/long wear has been silicone chemistry. In the texture category, silicone elastomers have superior cushioning and rheology profiles, with the main drawback of having a high amount of transfer. In the long wear category, silicone resins have been the primary film former in the cosmetics field, with the main drawback of being sticky and tacky on the skin. In addition, the use of silicone resins and elastomers with high amounts of water in the cosmetic formulations give problematic issues in term of stability.

Water-insoluble reaction product of a polyamine (polyethylemeimine (PEI)) and an oil-soluble polar modified polymer were previously described, for example, in U.S. 2010/0330024. Experience demonstrated that emulsions containing such reaction products has a maximum water content of up to 45%. Increased water-content resulted in emulsion separation.

It remains desirable to provide cosmetic compositions, particularly makeup compositions, which employ emulsions that having excellent stability, high water content, and long-wear properties without silicone resins.

SUMMARY OF THE INVENTION

The present invention relates to emulsions comprising an anhydrous solvent-in-oil (S/O) emulsion comprising at least one oil-soluble polar modified polymer and at least one polylysine. Preferably, the emulsions are substantially free of silicone resins.

The present invention also relates to colored emulsions comprising an anhydrous solvent-in-oil (S/O) emulsion comprising at least one coloring agent, at least one oil-soluble polar modified polymer, and at least one polylysine. Preferably, the emulsions are substantially free of silicone resins. Such colored emulsions can be in the form of cosmetic compositions such as, for example, lip compositions (for example, lipstick or liquid lip colors), foundations or mascaras.

The present invention also relates to methods of treating, caring for and/or making up keratinous material (for example, skin, eyes, eyelashes or lips) by applying compositions/emulsions of the present invention to the keratinous material in an amount sufficient to treat, care for and/or make up the keratinous material.

The present invention further relates to covering or hiding skin defects associated with keratinous material (for example, skin or lips) by applying compositions/emulsions of the present invention to the keratinous material in an amount sufficient to cover or hide such skin defects.

The present invention also relates to methods of enhancing the appearance of keratinous material (for example, skin, eyelashes, or lips) by applying compositions/emulsions of the present invention to the keratinous material in an amount sufficient to enhance the appearance of the keratinous material.

The present invention further relates to compositions/emulsions having improved cosmetic properties such as, for example, stability, increased anti-smudging properties, increased long wear properties and/or better texture or feel upon application.

The present invention also relates to methods of increasing both the anti-smudging properties and long wear properties of a composition/emulsion comprising adding to a composition/emulsion at least one oil-soluble polar modified polymer and at least one polylysine. Preferably, the composition/emulsion is substantially free of silicone resin.

The present invention also relates to methods of making a composition/emulsion comprising adding at least one oil-soluble polar modified polymer, at least one polylysine and at least one solvent to form a composition/emulsion. Preferably, the composition/emulsion is substantially free of silicone resin.

The present invention further relates to methods of making a composition/emulsion comprising mixing at least one oil-soluble polar modified polymer, at least one surfactant, at least one polylysine and at least one anhydrous solvent to form a first emulsion; and mixing the first emulsion with water to yield a water-in-oil emulsion.

It has been surprisingly discovered that the above-described compositions/emulsions are stable over time (little or no separation and/or creaming). By using a polylysine instead of PEI, S/O emulsions with an anhydrous colloidal system can be achieved. The emulsions are stable over time, with little or no separation and/or creaming. Moreover, the films produced by application of these emulsions to keratinous materials are water- and oil-resistant, and have nice texture and pleasant feel.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about."

"Anhydrous," as used herein, means a water content of less than or equal to 3% by weight, for example, less than 2% by weight or less than 1% by weight, relative to the weight of the composition, including 0% water. If present, water in the composition may be "bound water," for instance the water of crystallization of salts, or traces of water absorbed by the starting materials used in the preparation of the anhydrous compositions according to the present disclosure.

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Keratinous substrates", as used herein, include but are not limited to, skin, hair, eyelashes, lips and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Substantially free" as used herein means that the emulsion compositions described herein contain less than about 1% by weight of the composition of the identified compound such as, for example, silicone resins and/or surfactants. The emulsion compositions can also contain less than about 0.5% by weight of the composition, more preferably less than about 0.01% by weight of the composition, and preferably 0% of identified compounds such as silicone resins and/or surfactants (all of which are compassed within the meaning of "substantially free").

"Volatile", as used herein, means having a flash point of less than about 100° C. "Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Emulsions comprising a solvent-in-oil emulsion" include emulsions such as, for examples, a solvent-in-oil emulsion, a solvent-in-oil-in-water emulsion, etc.

Oil-Soluble Polar Modified Polymer

According to the present invention, compositions comprising at least one oil-soluble polar modified polymer are provided. "Oil-soluble polar modified polymer" as used herein refers to "oil-soluble low carbon polar modified polymers" and/or "oil-soluble high carbon polar modified polymers.

Oil-Soluble Low Carbon Polar Modified Polymer

According to the present invention, compositions comprising at least one oil-soluble low carbon polar modified polymer are provided. "Low carbon polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decane, isodecane, and octadecane, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the low carbon polar modified polymer is oil-soluble: that is, the polymer does not contain a sufficient amount of hydrophilic unit(s) to render the entire polymer water-soluble or oil-insoluble. According to preferred embodiments, the low carbon polar modified polymer contains the same amount of hydrophobic monomer as hydrophilic unit (1:1 ratio) or more hydrophobic monomer than hydrophilic unit. According to particularly preferred embodiments, the low carbon polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the low carbon polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the low carbon polar modified polymer is a wax. According to particularly preferred embodiments, the low carbon polar modified wax is made via metallocene catalysis, and includes polar groups or units as well as a hydrophobic backbone. Suitable modified waxes include those disclosed in U.S. patent application publication No. 20070031361, the entire contents of which is hereby incorporated by reference. Particularly preferred polar modified waxes are C2-C3 polar modified waxes.

In accordance with preferred embodiments of the present invention, the low carbon polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the low carbon polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Low carbon polar modified waxes can be produced in a known manner from the homopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable low carbon polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA." "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the low carbon polar modified polymer is not a wax. In accordance with these embodiments of the present invention, the low carbon polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the low carbon polar modified polymer can be of any form typically associated with polymers such as, for example, block copolymer, a grafted copolymer or an alternating copolymer. For example, the low carbon polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil soluble low carbon polar modified polymer(s) represent from about 1% to about 70% of the total weight of the composition, more preferably from about 5% to about 60% of the total weight of the composition, and most preferably from about 15% to about 50%, including all ranges and subranges therebetween.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the LicoCare name having designations such as CM 401, which is a maleic anhydride modified wax having a Mw of 2025 and a crystallinity of 11%, C30-C38 olefin/isopropyl-maleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil soluble high carbon polar modified polymer(s) represent from about 1% to about 50% of the total weight of the composition, more preferably from about 5% to about 60% of the total weight of the composition, and most preferably from about 15% to about 50%, including all ranges and subranges therebetween.

Polylysine

According to the present invention, emulsions further comprising polylysine are provided. Polylysine is well known. Polylysine can be a natural homopolymer of L-lysine that can be produced by bacterial fermentation For example, polylysine can be ε-Poly-L-lysine, typically used as a natural preservative in food products. Polylysine is a polyelectrolyte which is soluble in polar solvents such as water, propylene glycol and glycerol. Polylysine is commercially available in various forms, such as poly D-lysine and poly L-lysine. Polylysine can be in salt and/or solution form.

Preferably, the polylysine is present in an amount of 0.01 to 20% of the total weight of the emulsion composition, including 0.05 to 15% and 0.1 to 10% by weight, including all ranges and subranges therebetween.

Reaction Product

According to preferred embodiments of the present invention, the oil-soluble polar modified polymer is reacted with the polylysine compound, in the presence of solvent in, at minimum, an amount sufficient to solubilize the polylysine, to form a reaction product. In accordance with the preferred embodiments, the reaction product is water-insoluble and/or solvent-insoluble.

Although not wanting to be bound by any particular theory, it is believed that at a temperature below 100° C., the reaction of the oil-soluble polar modified polymer with the polylysine opens the anhydride ring to form a half acid and half amide crosslinked product. However, at a temperature above 100° C., the reaction of the oil-soluble polar modified polymer with the polylysine opens the anhydride ring to form an imide crosslinked product. The former product is preferred over the latter product. It is not necessary for all amine groups and all hydrophilic groups to react with each other to form the reaction product. Rather, it is possible that the composition may contain free polylysine and/or free oil-soluble polar modified polymer in addition to the reaction product.

Although not wanting to be bound by any particular theory, it is also believed that the polylysine(s) can be non-covalently assembled with the polar modified polymer(s) by electrostatic interaction between an amine group of the polylysine and a hydrophilic group (for example, carboxylic acid group associated with maleic anhydride groups) of the oil-soluble polar modified polymer to form a supramolecule. For example, with specific reference to maleic anhydride groups, in the presence of anhydrous solvent these groups can open to form dicarboxylic acid groups which can interact with protonated primary amines of the polylysine through ionic interaction to form a polymer-polymer complex with hydrophilic core crosslinkers and a hydrophobic network that act as supramolecular capsule. If a large amount of maleic anhydride groups are present, further primary amine groups of polylysine are also protonated and interact with alkyl carboxylates.

According to preferred embodiments, the oil-soluble polar modified polymer is in an oil carrier, and the polylsyine compound is in an anhydrous solvent carrier, and the reaction occurs by combining the oil carrier and the solvent carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polylysine, the subsequent reaction product that is formed is surprisingly and unexpectedly able to entrap large amounts of anhydrous solvent molecules within its hydrophobic matrix. The resultant product is eminently capable of forming a film, is self-emulsifying, waterproof. Moreover, the product is both stable and capable of carrying various types of ingredients.

Anhydrous Solvent

The emulsions of the present invention also contain anhydrous solvent. Preferably, the anhydrous solvent is a polar solvent. More preferably, the anhydrous solvent is a polyol. Such polyols are well-known in the cosmetic field and may include, for example, ethylene glycol, propylene glycol, polyethylene glycol, polypropylene glycol, glycerol or a combination thereof.

The anhydrous solvent is preferably present in an amount of from about 0.1% to about 80% by weight, preferably 5% to about 60% by weight, preferably about 15% to about 50% by weight, including all ranges and subranges therebetween, all weights being based on the total weight of the composition.

Surfactant

According to the present invention, emulsions optionally further comprising at least one surfactant are provided. In accordance with such embodiments of the present invention, any suitable surfactant for use in water-in-oil emulsions can be used. Such surfactants are well-known in the field.

According to preferred embodiments, at least one surfactant having an HLB value greater than or equal to 10 is present in the emulsion. Preferably, the at least one surfactant has an HLB value of 10-17, preferably 11-17, including all ranges and subranges therebetween. Examples of suitable surfactants include, but are not limited to, PEG-40-stearate and PEG-8-stearate. Any suitable surfactants for forming emulsions, including a water-in-oil-in-water emulsion, can be used in accordance with the present invention. In addition to alkoxlated/fatty acid surfactants discussed above such as the PEG/fatty acid surfactants (which would include, but not be limited to, PEG amounts ranging from 1 to about 100, 3 to about 75, and 8 to about 40, including all ranges and subranges therebetween, and would also include but not be limited to fatty acid components having from 8 to about 32 carbons, from 10 to about 24 carbons, and from 12 to about 18 carbons, including all ranges and subranges therebetween such as, e.g., stearate, oleate, myristate, palmitate, etc.), If present, the at least one surfactant may be present in amounts from 0 to 20% of the total weight of the composition, preferably 0.05 to 10%, and preferably 0.1 to 5%, including all ranges and subranges therebetween.

Volatile Oil

According to particularly preferred embodiments of the present invention, compositions optionally further comprising at least one volatile oil are provided. Preferably, the at least one volatile oil is a silicone volatile oil, a hydrocarbon volatile oil, or a mixture thereof.

According to preferred embodiments, the composition may contain one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the composition may contain one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, isohexadecane, and for example, the oils sold under the trade names of Isopar or Permethyl, the C8 to C16 branched esters such as isohexyl or isodecyl neopentanoate and their mixtures. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839.

Preferably, the volatile oil(s), when present, represent from about 5% to about 90% of the total weight of the composition, more preferably from about 10% to about 80% of the total weight of the composition, and most preferably from about 20% to about 75%, including all ranges and subranges therebetween.

Coloring Agents

According to particularly preferred embodiments of the present invention, compositions optionally further comprising at least one at least one coloring agent are provided. Preferably, such colored compositions are cosmetic compositions such as, for example, lip compositions (for example, lipstick or liquid lip colors), mascaras, nail polish or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Film Forming Agents

According to particularly preferred embodiments of the present invention, compositions optionally further comprising at least one at least one film forming agent (film former) are provided. Acceptable film forming agents are known in the art and include, but are not limited to, those disclosed in U.S. patent application publication No. 2004/0170586, the entire contents of which is hereby incorporated by reference. Non-limiting representative examples of such film forming agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

According to preferred embodiments, the film former, when present, is present in the composition in an amount ranging from 0.1% to 30% by weight relative to the total weight of the composition. Preferably, the film former is present in an amount ranging from 0.5% to 20% by weight relative to the total weight of the composition, and more preferably from 2% to 15%, including all ranges and subranges therebetween. One of ordinary skill in the art will recognize that the film former of the present invention may be commercially available, and may come from suppliers in the form of a dilute solution. The amounts of the film former disclosed herein therefore reflect the weight percent of active material.

According to particularly preferred embodiments, when a film forming agent is present, the combined amount of the amount of oil-soluble polar modified polymer and the film forming agent is 30-50% by weight of the entire weight of the composition.

However, in other preferred embodiments of the present invention, the emulsion composition is substantially free of silicone resin (that is, less than 1% of silicone resin) or essentially free of silicone resin (that is, less than 0.5% silicone resin). According to a particularly preferred embodiment, the emulsion contains no silicone resin.

Another particularly preferred embodiment of the present invention is a composition for application to keratin materials (hair or eyelashes) which is an emulsion but which is substantially free of triethanolamine/stearate (TEA-stearate) (that is, less than 1% of TEA-stearate) or free of TEA Stearate (that is, less than 0.05% TEA-stearate).

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, pasty compounds and mixtures thereof can be added. A non-exhaustive listing of such ingredients can be found in U.S. patent application publication No. 2004/0170586, the entire contents of which is hereby incorporated by reference. Further examples of suitable additional components can be found in the other references which have been incorporated by reference in this application. Still further examples of such additional ingredients may be found in the International Cosmetic Ingredient Dictionary and Handbook (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

Non-limiting examples of such additional components include non-volatile oils such as silicone oils (for example, dimethicone, phenyl trimethicone, trimethyl pentaphenyl trisiloxane, etc) or hydrocarbon oils (for example, esters). In one embodiment of the present invention, the compositions of the present invention are substantially free of silicone oils (i.e., contain less than about 1% silicone oils). In another embodiment, the compositions are substantially free of non-silicone oils (i.e., contain less than about 1% non-silicone oils). In another embodiment, the compositions are substantially free of non-volatile oils (i.e., contain less than about 1% non-volatile oils).

According to preferred embodiments of the present invention, methods of treating, caring for and/or making up keratinous material such as skin, lips, hair and mucous membranes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention comprising at least one oil-soluble polar modified polymer and at least one polylysine are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 3 minute or less, more preferably for about 2 minutes or less. The composition is preferably applied to the desired area that is dry or has been dried prior to application, or to which a basecoat has been previously applied.

According to a preferred embodiment of the present invention, compositions having improved cosmetic properties such as, for example, improved stability, improved feel upon application (for example, texture, reduced drag or tackiness), increased anti-smudging properties, and/or increased long wear properties are provided.

According to other embodiments of the present invention, methods of improving the anti-smudging, transfer-resistance and/or long wear properties of a composition, comprising adding at least one oil-soluble polar modified polymer and at least one polylysine to the composition are provided. In accordance with this embodiment, the at least one oil-soluble polar modified and the at least one polylysine are present in amounts sufficient to achieve the desired result.

According to yet other embodiments of the present invention, methods of making a composition comprising mixing together at least one polylysine and at least one oil-soluble polar modified polymer to form a composition are provided.

In accordance with preferred embodiments, S/O emulsions are prepared in a process that includes reactive emulsion technology. The technology is versatile in that allows producing S/O emulsions. Using such reactive emulsion technology, it is believed that chemical crosslinking of the at least one oil-soluble polar modified polymer and the at least one polylysine occurs at the solvent-oil interface in the emulsion, allowing the emulsions with various ranges of properties (e.g., rheology and water content) to be achieved. Further, it is believed that such technology facilitates regulating the size of the dispersed phase(s) as well as the solvent content in the water phase.

By varying the relative amounts of the oil-soluble polar modified polymer and polylysine, liquids and gels of different hardness can be obtained. Moreover, films produced from the emulsions/compositions of the present invention are both water- and oil-resistant, and demonstrate nice texture and pleasant feel. This makes these systems particularly suitable for long wear cosmetic products.

According to preferred embodiments, an anhydrous emulsion (S/O) can be further processed by combining the anhydrous emulsion with water, and then mixing these components to form a stable emulsion. Such emulsions can demonstrate liquid-like behavior.

According to preferred embodiments, an oil phase containing the at least one oil-soluble polar modified polymer (e.g., Ethylene/maleic Anhydride/propylene Copolymer) and a solvent-phase containing the at least one polylysine are combined to form an S/O emulsion such that polylysine reacts with the at least one oil-soluble polar modified polymer to form a reaction product. It is believed that this reaction product is facilitated by physical and/or chemical crosslinking discussed above, and occurs depending on the processing conditions. It is believed, at least as a partial result of such crosslinking, solvent is entrapped in the crosslinked oil-soluble polar modified polymer polymer/polylysine reaction product, which is surrounded by the oil phase.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

An anhydrous liquid emulsion is prepared with the following ingredients:

| Phase | Name | Conc. % |
|---|---|---|
| A | Isohexadecane (IHD) | 84.0 |
| A | Ethylene/maleic Anhydride/propylene Copolymer (PPMA)100% by solid | 15.0 |
| B | Propylene glycol | 0.5 |
|   | polylysine | 0.5 |
|   | Total | 100 |

Each of phase A-B are separately prepared and mixed in a beaker with stirring for 30 minutes at 80° C. until a stable emulsion is obtained. The final product is a liquid.

A liquid emulsion is prepared by mixing 80% by weight of the composition with 20% water until a stable emulsion is obtained.

Example 2

S/O emulsion: elastic gel

| Phase | Name | Conc. % |
|---|---|---|
| A | Isohexadecane (IHD) | 59.4 |
| A | Ethylene/maleic Anhydride/propylene Copolymer (PPMA)100% by solid | 30.0 |
| B | Propylene glycol | 5.3 |
|   | polylysine | 5.3 |
|   | Total | 100 |

Each of phase A and phase B are separately prepared and mixed in a beaker with stirring at 80° C. for 30 minutes until a stable emulsion is obtained. The final product is an elastic gel.

Example 3

W/O emulsion produced from S/O emulsion

| Phase | Name | Conc. % |
|---|---|---|
| A | Isohexadecane (IHD) | 6.7 |
| A | Ethylene/maleic Anhydride/propylene Copolymer (PPMA)100% by solid | 12 |
| B | Propylene glycol | 0.4 |
| B | polylysine | 0.4 |
| C | water | 20.0 |
|   | Total | 100 |

Each of phase A and phase B are separately prepared and mixed in a beaker with stirring at 80° C. for 30 minutes until a stable emulsion is obtained. In the next step, the phase C (water) is slowly added to the s/o emulsion formed under stirring at room temperature and mixed until a stable w/o emulsion is obtained.

Example 4

Liquid Foundation

| Phase | Name | Conc. % |
|---|---|---|
| A | isododecane | 29.6 |
| A | Dodecamethylpentasiloxane | 12 |
| A | Ethylene/maleic Anhydride/propylene Copolymer (PPMA)100% by solid | 10 |
| B | Propylene glycol | 0.8 |
| B | polylysine | 0.8 |
| B | Pigment grid | 13.2 |
| B | Sunsphere silica | 3 |
| B | Polymethysilsesquioxane | 3 |
| C | Water | 20 |
| C | Disodium edta | 0.2 |
| C | Propylene glycol | 1.0 |
| C | Phenoxyethanol | 0.7 |
| C | Chlorphenesine | 0.2 |
| C | Sodium chloride | 0.5 |
| D | Ethanol | 5.0 |
| | Total | 100 |

Each of phase A and phase B are separately prepared and mixed in a beaker with stirring at 80° C. for 30 minutes until a stable emulsion is obtained. In the next step, the phase C is slowly added under stirring and mixed until the stable w/o emulsion is obtained, followed by adding ethanol at room temperature.

What is claimed is:

1. An anhydrous solvent-in-oil emulsion comprising:
   (a) an anhydrous solvent selected from the group consisting of glycerol, propylene glycol, butylene glycol, and mixtures thereof;
   (b) polylysine; and
   (c) polar modified polymer comprising C2-C4 monomer and modified with maleic anhydride unit, and having a weight-average molecular weight of less than or equal to 25 000 g/mol and a melting point above 75° C.

2. The anhydrous solvent-in-oil emulsion of claim 1, further comprising at least one coloring agent.

3. The anhydrous solvent-in-oil emulsion of claim 1, wherein the anhydrous solvent-in-oil emulsion is made using from 0.01 to 20% by weight, based on the weight of the anhydrous solvent-in-oil emulsion, of the polylysine.

4. The anhydrous solvent-in-oil emulsion of claim 1, wherein the anhydrous solvent-in-oil emulsion is made using from 0.05 to 15% by weight, based on the weight of the anhydrous solvent-in-oil emulsion, of the polylysine.

5. The anhydrous solvent-in-oil emulsion of claim 1, wherein the anhydrous solvent-in-oil emulsion is made using from 1 to 70% by weight, based on the weight of the anhydrous solvent-in-oil emulsion, of the polar modified polymer.

6. The anhydrous solvent-in-oil-emulsion of claim 1, further comprising at least one surfactant.

7. A cosmetic composition comprising the anhydrous solvent-in-oil emulsion of claim 1.

8. A method of making up skin comprising applying to the skin the anhydrous solvent-in-oil of claim 6.

9. A method of making up lips comprising applying to the lips the anhydrous solvent-in-oil of claim 6.

10. A method of making up eyelashes comprising applying to the eyelashes the anhydrous solvent-in-oil of claim 6.

* * * * *